(12) United States Patent
Kobayashi

(10) Patent No.: US 6,526,319 B2
(45) Date of Patent: Feb. 25, 2003

(54) LIVING BODY STIMULATING APPARATUS

(76) Inventor: Tatsuyuki Kobayashi, c/o Techno Link Co., Ltd. of 8-12, Ariakeohhashi-cho, Niigata-shi, Niigata-ken (JP)

( * ) Notice: Subject to any disclaimer, the term of this patent is extended or adjusted under 35 U.S.C. 154(b) by 71 days.

(21) Appl. No.: 09/790,472

(22) Filed: Feb. 22, 2001

(65) Prior Publication Data

US 2001/0023362 A1 Sep. 20, 2001

(30) Foreign Application Priority Data

Mar. 17, 2000 (JP) ........................................ 2000-076884

(51) Int. Cl.$^7$ ................................................. A61N 1/18
(52) U.S. Cl. .............................. 607/72; 607/73; 607/74; 607/46; 607/58
(58) Field of Search .............................. 607/72, 73, 74, 607/46, 48, 50

(56) References Cited

U.S. PATENT DOCUMENTS

| | | | |
|---|---|---|---|
| 3,294,092 A | | 12/1966 | Landauer |
| 4,938,223 A | * | 7/1990 | Charters et al. ............. 128/421 |
| 5,018,524 A | | 5/1991 | Gu et al. |
| 5,097,833 A | * | 3/1992 | Campos ....................... 128/421 |
| 5,330,515 A | * | 7/1994 | Rutecki et al. ................ 607/46 |
| 5,397,338 A | | 3/1995 | Grey et al. |
| 5,836,081 A | | 11/1998 | Orosz, Jr. |

OTHER PUBLICATIONS

Japanese Patent Publication No. 1–146562; Published Jun. 8, 1989.

* cited by examiner

*Primary Examiner*—Teresa Walberg
*Assistant Examiner*—Shawntina T. Fuqua
(74) *Attorney, Agent, or Firm*—Akerman Senterfitt

(57) ABSTRACT

A living body stimulating apparatus for obtaining extensive therapeutic effects as well as soft feel of stimulation. Rectangular wave pulses output at a preset recurring frequency are subjected to pulse width modulation. Thus, the recurrence of a rectangular wave pulse group (S) which includes a plurality of higher frequency signal components than the rectangular wave pulses is imparted to a human body through electrodes (24). As a human body has a capacitive property, the higher frequency the signal component has, the lower impedance it will result in. As a result, the waveform of the rectangular wave pulse group (S) is distorted as a whole, thus providing softer feel of stimulation as compared with rectangular wave pulses of the same current and frequency. In addition, due to the higher frequency signals components being included, more extensive therapeutic effects can be expected.

20 Claims, 4 Drawing Sheets

F I G. 2
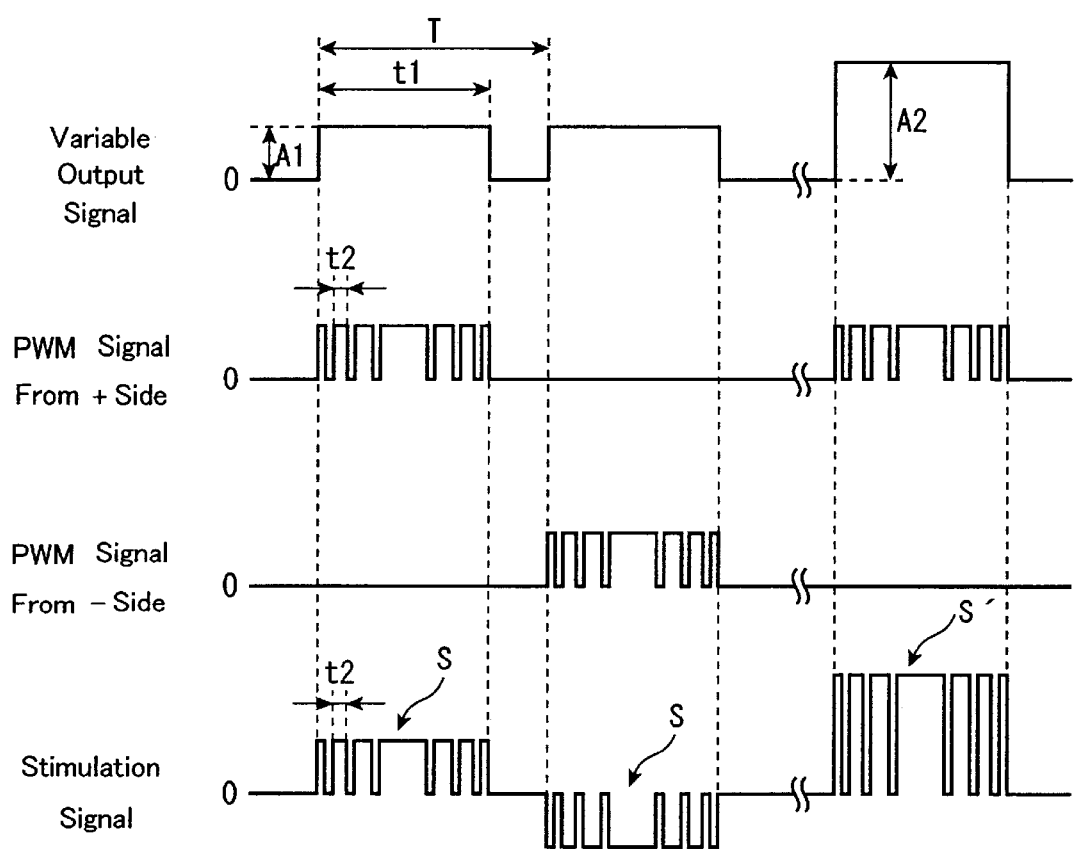

Waveform in a case a where the apparatus is connected to 500 Ω load,

Waveform in a case a where the apparatus is connected to a human waist

LIVING BODY STIMULATING APPARATUS

BACKGROUND OF INVENTION a) Field of Invention

The present invention relates to a living body stimulating apparatus, such as a low-frequency electro-therapeutic device, for stimulating a living body by attaching a conductor element with a built-in electrode to a living body to thereby allow electric current to flow through the electrode into the living body.

b) Prior Art

In general, such type of living body stimulating apparatus is aimed at the treatment of nerve function in a diseased part, by allowing a low frequency pulse current to flow in the diseased part, said low frequency pulse current being output from a transmitter to an electrode. In Japanese Patent Un-Examined Publication No.1-146562, for example, is disclosed a living body stimulating apparatus which enables the control of the speed and intensity of stimulation, by switching stimulation signals output from an output circuit to a living body (or human body) to either one of DC intermittent pulses for periodically outputting positive pulses, AC intermittent pulses for periodically outputting rectangular wave pulse groups consisting of positive pulses and negative pulses, and Alternate intermittent pulses for periodically and alternately outputting positive pulses and negative pulses, and/or by varying the period or amplitude of the respective intermittent pulses.

In the meantime, a human body is generally hard to pass an electric direct current therethrough, which has a resistance of about 100 kΩ that varies depending upon voltage, whilst an alternate electric current of high-frequency is relatively easy to flow through a human body. For example, a human body indicates a resistance of about 1 kΩ under an AC voltage of 1 kHz, said resistance being reduced by half if a frequency doubles. In other words, a human body has a sort of a capacitance like that of a capacitor, so that it has a tendency to decrease in-vivo resistance as a frequency increases. On the other hand, from a standpoint of a feel of stimulus against a human body, low frequencies which are close to direct current, and rectangular waves involving many D.C. components (or straight portions) get more stimulative, and thus if a frequency is the same, sinusoidal waves will impart more moderate or softer stimuli than rectangular waves.

FIG. 5 illustrates an example of a conventional living body stimulating apparatus for imparting stimulation signals in the form of sine waves to a human body. In the drawing, numeral 101 designates CPU (central processing unit) as a control means, which outputs digital data signals which are then converted into analogue data signals by D/A circuit 102. Then, the analogue data signals are amplified by a amplifier circuit 103, to thereby make the sine-wavelike stimulation signals come out between conductive elements or output electrodes 105 across a transformer 104. In that case, the amplitude of the sine wave is capable of being freely increased or decreased by operating an output variable volume lOG connected to a front side of the amplifier 103.

Although such sinusoidal wave does impart a soft feel of stimulation and thus it is desirable to a human body, yet it includes a single frequency component only, thus leading to a great disadvantage in obtaining extensive therapeutic effects. Further, in an output circuit for use in such apparatus, socalled analogue circuits such as the D/A circuit 102 and the amplifier circuit 103 have to be used for obtaining a substantially sinusoidal waveform, and thus the number of components inevitably increases and the structure of circuits becomes more complex, thus leading to bad power efficiency. In other words, conventional circuits for output of sinusoidal waves would require dozens of components such as transistors, resistors and capacitors.

SUMMARY OF THE INVENTION

To eliminate the above problems, it is a main object of the invention to provide a living body stimulating apparatus which realizes extensive therapeutic effects with soft stimuli being imparted to a living body.

To attain the above objects, there is proposed a living body stimulating apparatus for imparting stimuli to a living body by attaching electrodes to the living body so as to pass electric current through the living body via the electrodes, which comprises: a stimulus generator for subjecting recurringly output rectangular wave pulses to pulse width modulation, and then outputting the recurrence of rectangular wave pulse groups serving as stimulation signals to the electrodes, each rectangular wave pulse group including a plurality of frequency components higher than said rectangular wave pulse.

It should be noted that the present invention has been made, focusing on the fact that a living body has a property similar to that of a capacitor. With the above-mentioned structure, when the stimulus generating means is allowed to modulate the width of rectangular pulses which are output at a predetermined recurrence frequency, then a living body is supplied with the recurrence of pulse groups each of which includes a plurality of signal components whose frequencies are higher than that of the rectangular wave pulse, said recurrence of pulse groups serving as stimulating signals supplied from the output electrodes. At that time of moment, as a living body has such a capacitor-like property, the higher frequency the signal component has, the lower impedance it will result in, so that the waveform of the rectangular pulse group is distorted as a whole, thereby generating softer feel of stimulation than ordinary rectangular wave pulses that have the same current and frequency. In addition, as each rectangular wave pulse group includes signal components of higher frequency than that of the original rectangular wave pulse, extensive therapeutic effects can be expected from such signal component of the higher frequency.

BRIEF DESCRIPTION OF THE DRAWINGS

Other objects, features and advantages of the invention will be apparent to those skilled in the art from the following description of the preferred embodiments of the invention, wherein reference is made to the accompanying drawings, of which:

FIG. 2 is a waveform diagram showing waveforms in respective parts of the apparatus of FIG. 1.

DESCRIPTION OF PREFERRED EMBODIMENTS

Hereinafter are described preferred embodiments of the present invention with reference to attached drawings.

Figure 1:
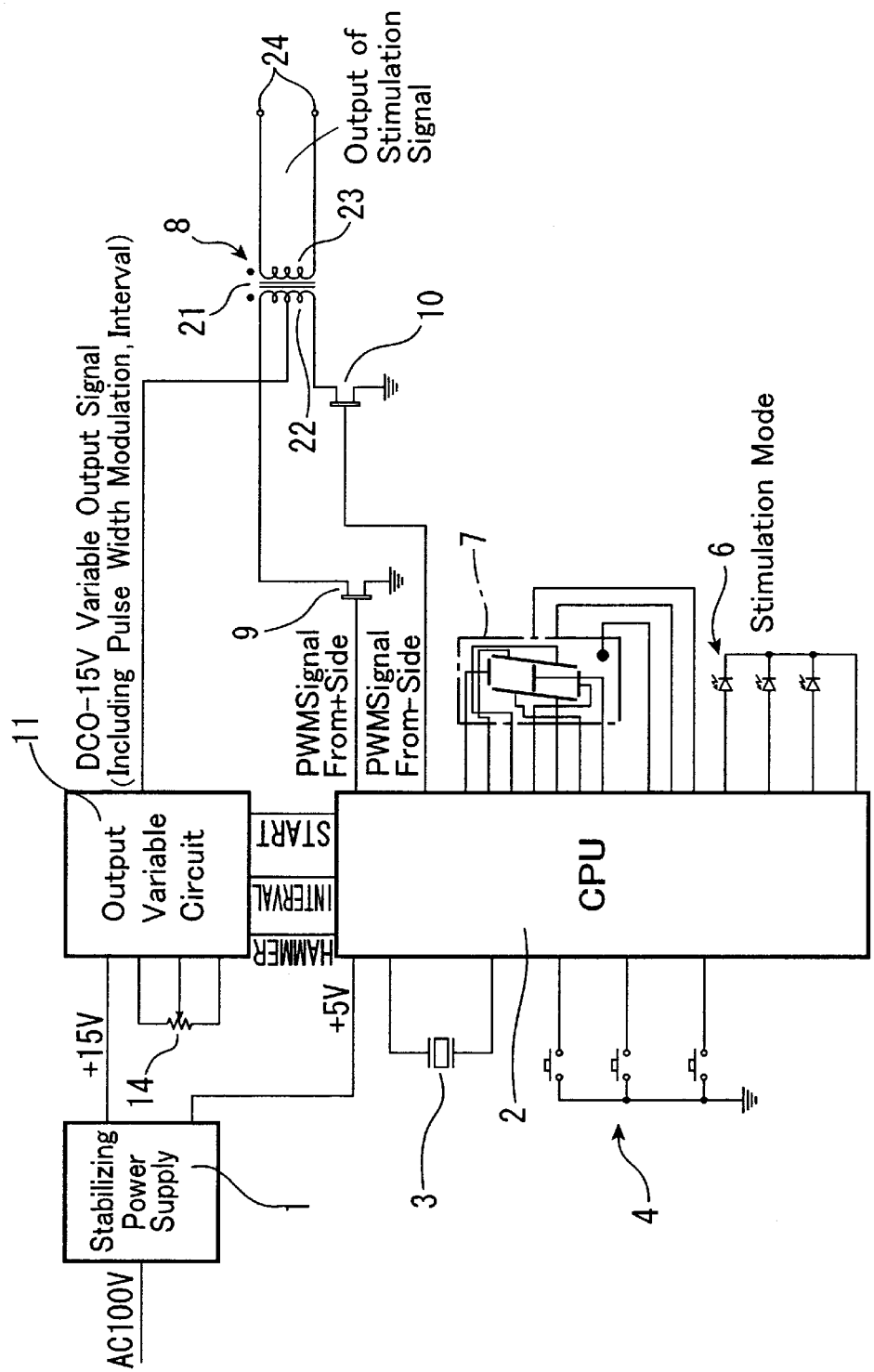
FIG. 1 is a circuit diagram showing a living body stimulating apparatus in accordance with a first embodiment of the invention.

First, an overall structure of an apparatus of the invention will be described with reference to FIG. 1. Reference numeral 1 designates a stabilizing power supply for converting AC input into DC output in a stable state. In the embodiment, AC voltage of AC 100 V is converted into DC voltages of DC+15V and DC+5V, respectively. Reference numeral 2 designates a CPU (central processing unit) which serves as a control means actuated by said DC+5V from the said stabilizing power supply 1 and reference clock signals from a crystal oscillator 3. The CPU 2 is, as is well known, integrated with an input/output means, a memory means, a processing means and the like, said memory means memorizing a control sequence, according to which are given predetermined patterns of stimulating electric currents to a human body (not shown)

To an input port of said CPU 2 are connected a plurality of switches 4 provided as a mode selection means for selecting a specific stimulation mode from among several stimulation modes. On the other hand, to an output port of said CPU 2 are connected a plurality of LEDs 6 provided as a display means for displaying which stimulation mode was selected and is being executed. Besides, to the output port of the CPU 2 are connected a segment LED 7 provided as a time display means for counting and displaying the stimulation time, two FETs 9, 10 which construct a stimulus generator means 8, and an output-variable circuit 11 for varying the amplitude and interval (pause) of stimulating signals to be imparted to a human body. For simplicity, only one segment LED 7 was illustrated in the present embodiment, but two or more segment LEDs 7 should actually be connected in parallel. Alternatively, the foregoing LEDs 6 and the segment LED 7 may be integrated together, by a common LCD display or the like.

The aforesaid output-variable circuit 11 is actuated by the DC voltage of DC+15V from the stabilizing power supply 1, so that respective control signals output from the CPU 2, namely, strong stimulation command (HAMMER) signal, stimulation pause (INTERVAL) setting signal, and stimulation start (START) signal, and an output level setting signal from a manually operable variable resistor 14 allow the stimulus generator means 8 to be supplied with variable output signals in rectangular waveforms which are output at a predetermined recurring frequency with the amplitude being modulated in a range of from DC 0V to DC+15V.

On the other hand, the aforesaid stimulus generator means 8 is aimed at subjecting the variable output signal from the output-variable circuit 11 to pulse width modulation, comprising the said FETs 9, 10 serving as the switching means and a transformer 21 of which primary and secondary sides are insulated from each other. Going into more detail, the primary winding 22 of the transformer 21 has a center tap connected to the variable output signal line of the said output-variable circuit 11, while the secondary winding 23 thereof for outputting the stimulating signals have ends connected to a pair of output electrodes 24 serving as conductive elements. Further, to a drain of the grounded source FET 9 is connected one end of the primary winding 22 of the transformer 21, while to a drain of the other source grounded FET 10 is connected the other end of the primary winding 22 of the transformer 21. Thus, +side PWM signals from the CPU 2 are supplied to a gate as a control terminal of the FET 9, while –side PWM signals from the CPU 2 are supplied to a gate as a control terminal of the FET 10.

Next, the action of the above-structured apparatus will be explained with reference to the waveform diagram of FIG. 2, in which the uppermost waveform shows a variable output signal from the output-variable circuit 11, followed by the respective waveforms of the +side PWM signals, –side PWM signals and stimulation signals between the output electrodes 24, in sequence.

If a specific stimulation mode is selected by the switch 4, and then a start switch (not shown) is operated, the LED 6 corresponding to the specific stimulation mode selected is lighted by the CPU 2. The CPU 2 also controls the respective parts including the stimulus generator means 8 and the output-variable circuit 11 in order that the stimulation signals that match the selected stimulation mode may be output between the output electrodes 24. Through such sequential control, the stimulation start signals are supplied from the CPU 2 to the output-variable circuit 11, and thus the variable-output signals are supplied from the output-variable circuit 11 to the stimulus generator means 8, said variable-output signals repeatedly outputting the rectangular pulses defining an amplitude A1 and predetermined time width t1, at every period T, as shown in FIG. 2. In the meantime, the amplitude A1 can be varied by the variable resistor 14, in a range of from DC0V to DC+15V, and thus it is possible for a user to change the degree of stimulation to a desired level. Although not shown in the drawings, if the period T and the time width ti also are made variable by the command from the CPU 2, it would be easier for a user to obtain more desirable stimulus, which would be easily realized by varying the control :program inside the CPU 2.

Every time the rectangular wave pulse is output from the said output-variable circuit 11, the CPU 2 is allowed to output on-pulses alternately to the FET 9 or FET 10, during the output period of the rectangular pulse, said on-pulse having a higher frequency component than the rectangular pulse. At that time of moment, the time width t2 of each on-pulse to the FET 9 or FET 10 is gradually expanded until one half of the time width t1 of the rectangular wave pulse elapses after the rise of the rectangular wave pulse, while each time width t2 thereof is gradually narrowed as the rectangular wave pulse approaches its break.

Then, when the +side PWM signal is supplied from the CPU 2 to the FET 9 with the rectangular wave pulse being output to the center tap of the primary winding 22 of the transformer 21, the FET 9 is turned on during the output period of the on-pulse, so that the primary side (i.e., dotted side) of the primary winding 22 is grounded, thus inducing a voltage in the primary side (dotted side) of the secondary winding 23. Likewise, when the –side PWM signal is supplied from the CPU 2 to the FET 10 with the rectangular wave pulse being output to the center tap of the primary winding 22 of the transformer 21, the FET 10 is turned on during the output period of the on-pulse, so that the secondary side (i.e., non-dotted side) of the primary winding 22 is grounded, thus inducing a voltage in the secondary side (non-dotted side) of the secondary winding 23. Accordingly, as shown in FIG. 2, the supply of the on-pulses to the gate of the FET 9 during the output period of the rectangular wave pulses allows positive-polarized stimulation signals to be output in the form of pulse, while the supply of the on-pulses to the gate of FET 10 during the output period of the rectangular wave pulses allows negative-polarized stimulation signals to be output in the form of pulse.

Thus, between the output electrodes 24 are repeatedly generated the stimulation signal of which the voltage level is proportional to the amplitude A1, said signals being obtained by subjecting the rectangular wave pulses of the variable-output signals to pulse width modulation (PWM) through the FETs 9, 10. These stimulation signals are constructed of a group S of the rectangular wave pulses which is generated every period T, having the time width t1, said rectangular wave pulse group S alternating between the positive and the negative. Further, the time width t2 of each on-pulse is gradually expanded until one half of the time width t1 of the rectangular wave pulse group S elapses after the rise thereof, while each time width t2 thereof is gradually narrowed as the group S approaches its break. In the meantime, as long as the stimulation signal is output, a built-in timer (not shown) inside the CPU 2 is allowed to count time, and displays the time on the segment LED 7.

Figure 3:
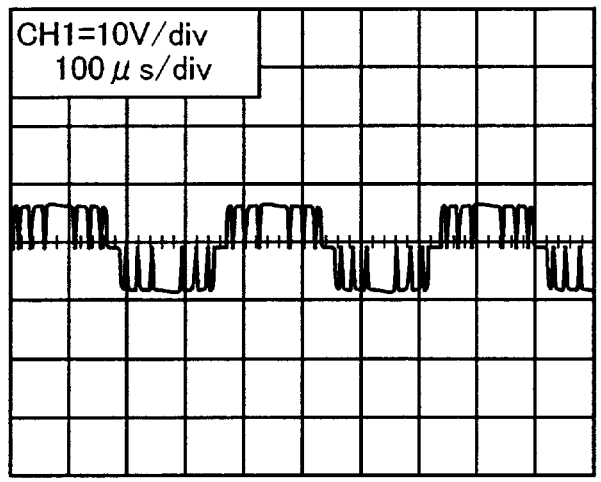
FIG. 3 is a waveform diagram of a stimulating signal in a case where a dummy resistance is connected to between output electrodes of the apparatus.
Figure 4:
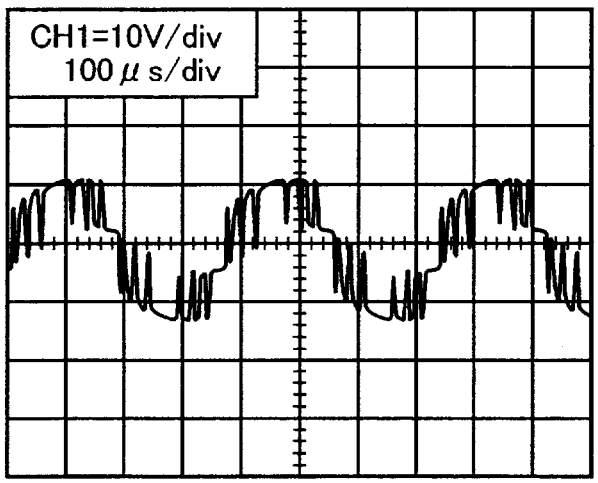
FIG. 4 is another waveform diagram of a stimulating signal in a case a human waist is attached to between the output electrodes of the apparatus.
Figure 5:
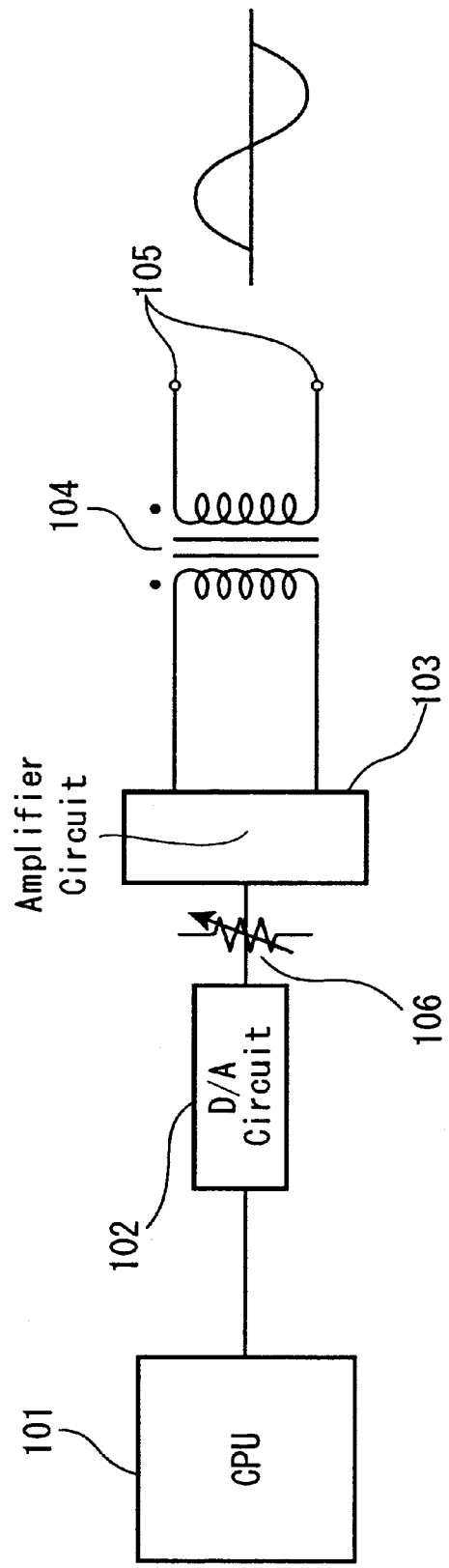
FIG. 5 is a circuit diagram showing a principal part of prior art.

FIG. 4 shows a waveform diagram of such stimulation signals that are actually imparted to a human body. The stimulation signal adopted here to represent a sample waveform defines a rectangular wave pulse of which the recurring frequency is 2.8 kHz (T=357 μSec), including high frequency components of which the time width t2 is variable in a range of from 10 to 60 Sec. FIG. 3 shows a comparative waveform in a case where a 500Ω dummy resistor is connected as a load between the output electrodes 24. In that case, substantially the same waveform as that of the stimulation signal of FIG. 2 is generated between the terminals of the dummy resistor. In contrast, FIG. 4 shows a waveform in a case where the output electrodes 24 are attached to a human waist and then it is energized. In that case, a human body functions as if it were a capacitive element of a capacitor, so that the waveform of each rectangular wave pulse group S is so distorted that the stimulation signal takes a waveform similar to a sinusoidal wave of a low frequency. Accordingly, extremely soft feel of stimulation can be obtained as compared with rectangular waves of the same frequency and current. Furthermore, as in the stimulation signals remain the high frequency components obtained by the switching of the FETs 9 and 10, the therapeutic effects by such high frequency components also can be expected.

In the meantime, in order to approximate the waveform of the stimulation signals to the sinusoidal wave as illustrated in FIG. 4 when applying the stimulation signals to a human body, it is desirable to construct the stimulus generator means 8 so that each rectangular pulse group S consisting of a plurality of on-pulses, defining the time width t1, may alternately appear between the positive side and the negative side, at intervals of the period T, and that the time width t2 of each on-pulse is gradually expanded until one half of the time width t1 of the rectangular wave pulse group S elapses after the rise thereof, while each time width t2 thereof is gradually narrowed as the rectangular wave pulse approaches the break of the group S. It should be noted, however, that if a time width variable means for varying the time width t2 of the on-pulse is added to for example the control sequence of the CPU 2, then various waves such as triangular waves or distorted waves besides the sinusoidal waves can be applied to a human body, thus enabling a unique feel of stimulation different from that by the sinusoidal wave to be obtained.

Whereas, when the above-mentioned stimulation signals are repeatedly applied to a human body, there is one drawback noted such that it will soon or later get accustomed to the stimulation signals, so that the therapeutic effects such as the removal or alleviation of pains, are gradually lowered. Therefore, in a preferred form of the invention, as a part of the control sequence of the CPU 2, the output of the stimulation signals is temporarily stopped during the output of the stimulation pause setting signal from the CPU 2 to the output variable circuit 11 so as to provide a stimulation pause period, or otherwise, when the strong stimulation command signal is output from the CPU 2 to the output variable circuit 11, a rectangular pulse whose amplitude A2 is greater than the predetermined amplitude A1 is temporarily output from the output variable circuit 11 to the stimulus generator means 8, thus imparting to a human body stronger stimulation signals having rectangular wave pulse group S' of greater amplitude, so that the above-mentioned drawback is eliminated.

As is apparent from the foregoing, a living body stimulating apparatus according to the embodiment of the invention comprises: the output electrodes 24 to be attached to a human body for stimulating the same by allowing electric current to flow therethrough from the electrodes 24; and the stimulus generator means 8 which modulates the pulse width of the rectangular wave pulse output at a predetermined recurring frequency, and then outputting the recurrence of the rectangular wave pulse group S serving as the stimulation signals to the electrodes 24, said rectangular wave pulse group S including a plurality of higher frequency components than the rectangular wave pulse.

In that case, if the stimulus generator means 8 modulates the pulse width of the rectangular wave pulse output at the predetermined recurring frequency, then the recurrence of the rectangular wave pulse group S including a plurality of higher frequency signal components than the rectangular wave pulse is imparted as stimulation signals through the output electrodes 24 to a human body. At that time of moment, due to a human body having such a capacitor-like property as above discussed, the higher frequency the signal component has, the lower impedance it will result in, so that the waveforms of the rectangular pulse groups are distorted as a whole, thereby generating softer feel of stimulation as compared with the rectangular wave pulses that have the same current and frequency. In addition, as each rectangular pulse group S includes signal components of higher frequency than that of the rectangular wave pulse, extensive therapeutic effects can be expected from such signal components of the higher frequency.

Moreover, the stimulus generator means 8 of the invention comprises the FETs 9 and 10 serving as switch means for on-off control of the rectangular wave pulse to thereby produce the rectangular wave pulse group S which includes the signal components having higher frequency than the rectangular wave pulse; and the CPU 2 serving as pulse width control means for supplying the FETs 9 and 10 with PWM digital signals (or +side PWM signals and –side PWM signals) for switching the FETs 9, 10.

With the structure thus made, to distort each rectangular wave pulse group of the stimulation signals, you have only to supply either on or off PWM digital signals to the FETs 9, 10 serving as switch means, thereby eliminating the need for conventional analogue circuit (such as the conventional D/A circuit 102 and the amplifier circuit 103) for obtaining the sinusoidal waveform. As a result, whilst conventional circuit for outputting sinusoidal waves would require dozens of components such as transistors, resistors and capacitors, the apparatus according to the present embodiment of the invention only requires a pair of FETs 9, 10 instead of such components, thus extremely simplifying the structure of the stimulus generator means 8 serving as the stimulation signal output circuit. Further, the pulse width modulation using the switch means indicates very high power efficiency, as have been demonstrated by motor inverters.

Besides, the CPU 2 of the embodiment of the invention comprises the strong stimulation command means for allowing the stimulus generator means 8 to output the rectangular wave pulse whose amplitude A2 is greater than the predetermined amplitude A1 thereof, and thus the strong stimulation command means enables the imparting of stronger stimulation signals having the rectangular wave pulse group S' of greater amplitude to a human body, whereby a human body is prevented from getting accustomed to the stimulation signals. Specifically, if the apparatus is so structured that the amplitude A2 of the rectangular wave pulse and/or the pause period of the stimulation signal may be randomly variable, then, a human body can be more effectively prevented from getting accustomed to the stimulation signals. In addition to the foregoing, as the foregoing strong signal command means, stimulation pause command means as well as the pulse width control means are all constructed by the control sequence of the CPU 2 serving as a common control means, there is an advantage that a circuit therefor needs less complicated structure.

The invention should not be limited to the foregoing embodiments, but may be modified within a scope of the invention. The recurring frequency of the rectangular wave pulse groups, the time width t1, t2 of the individual rectangular wave pulse group S, and the number of pulses of higher frequency signal components (on-pulse) may be varied comparatively freely, corresponding to the need therefor.

What is claimed:

1. A living body stimulating apparatus for applying an electrical stimulus to a living body comprising:
    electrodes attachable to the living body so as to allow electric current to flow through the living body via the electrodes; and
    a stimulus generator for generating stimulation signals from a periodic signal of a predetermined recurrence frequency by subjecting high-frequency recurrently output rectangular wave pulses to pulse width modulation, and then outputting the recurrence of rectangular wave pulse groups, serving as the stimulation signals, to the electrodes,
    wherein said pulse width modulated high-frequency pulses have their waveforms distorted by a capacitive function of the living body so that the stimulation signals take a low frequency waveform when said electrodes are attached to a living body.

2. A living body stimulating apparatus according to claim 1,
    wherein said stimulation signals are output such that each rectangular wave pulse group consists of a plurality of on-pulses, defining a predetermined time width of the pulse group as a whole, the pulses alternating between positive and negative signs periodically, and
    wherein the time width of each on-pulse is gradually increased during a first half of the predetermined time width of the pulse group, and is gradually decreased during a second half of the predetermined time width of the pulse group.

3. A living body Stimulating apparatus according to claim 1, wherein said stimulus generator comprises switch elements for on-off control of the rectangular wave pulses to thereby produce the rectangular wave pulse group which includes signal components having higher frequency than the rectangular wave pulse; and a pulse width control element for supplying the switch elements with PWM digital signals for switching the switch elements.

4. A living body stimulating apparatus according to claim 3, wherein said pulse width control element is constructed by a control sequence of a CPU.

5. A living body stimulating apparatus according to claim 1, further comprising a strong stimulation command element for temporarily outputting said rectangular wave pulses at a larger amplitude than at a predetermined one.

6. A living body stimulating apparatus according to claim 5, wherein said strong stimulation command element is constructed by a control sequence of a CPU.

7. A living body stimulating apparatus according to claim 1, further comprising a stimulation pause command element for temporarily stopping the output of said stimulation signals.

8. A living body stimulating apparatus according to claim 7, wherein said stimulation pause command element is so constructed that the pause period of the stimulation signals may be varied randomly.

9. A living body stimulating apparatus according to claim 7, wherein said stimulation pause command element is constructed by a control sequence of a CPU.

10. A living body stimulating apparatus according to claim 1, wherein the amplitude of said rectangular wave pulse is varied randomly.

11. A living body stimulating apparatus according to claim 1, wherein said periodic signal is a rectangular wave pulse signal consisting of rectangular pulses of a predetermined width, recurring at said predetermined recurrence frequency, and wherein the stimulation signal generator is adapted to generate groups of PWM pulses having said predetermined time width and sequentially alternating signs, the time width of a PWM pulse of a group gradually increasing during the first half of said group and gradually decreasing during the second half of said group.

12. A living body stimulating apparatus for applying an electrical stimulus to a living body comprising:
    electrodes attachable to the living body so as to allow electric current to flow through the living body via the electrodes; and
    a stimulus generator for generating stimulation signals by subjecting recurrently output rectangular wave pulses to pulse width modulation, and then outputting the recurrence of rectangular wave pulse groups serving as stimulation signals to the electrodes, each rectangular wave pulse group including a plurality of frequency components higher than said rectangular wave pulse;
    wherein said stimulation signals are output such that each rectangular wave pulse group consists of a plurality of on-pulses, defining a predetermined time width as a whole, the pulses periodically alternating between positive and negative signs,
    wherein the time width of each on-pulse gradually increases during a first half of said predetermined time width of the pulse group, and gradually decreases during a second half of said predetermined time width of the pulse group.

13. A living body stimulating apparatus according to claim 12, wherein said stimulus generator comprises: switch elements for on-off control of the rectangular wave pulses to thereby produce the rectangular wave pulse group which includes the signal components having higher frequency than the rectangular wave pulse; and a pulse width control element for supplying the switch elements with PWM digital signals for switching the switch elements.

14. A living body stimulating apparatus according to claim 13, wherein said pulse width control element is constructed by a control sequence of a CPU.

15. A living body stimulating apparatus according to claim 12, further comprising a strong stimulation command element for temporarily outputting said rectangular wave pulses at a larger amplitude than at a predetermined one.

16. A living body stimulating apparatus according to claim 15, wherein said strong stimulation command element is constructed by a control sequence of a CPU.

17. A living body stimulating apparatus according to claim 12, further comprising a stimulation pause command element for temporarily stopping the output of said stimulation signals.

18. A living body stimulating apparatus according to claim 17, wherein said stimulation pause command element is so constructed that the pause period of the stimulation signals may be randomly varied.

19. A living body stimulating apparatus according to claim 17, wherein said stimulation pause command element is constructed by a control sequence of a CPU.

20. A living body stimulating apparatus according to claim 12, wherein the amplitude of said rectangular wave pulse is randomly varied.

* * * * *

UNITED STATES PATENT AND TRADEMARK OFFICE
CERTIFICATE OF CORRECTION

PATENT NO. : 6,526,319 B2
DATED : February 25, 2003
INVENTOR(S) : Kobayashi

It is certified that error appears in the above-identified patent and that said Letters Patent is hereby corrected as shown below:

<u>Column 1,</u>
Line 59, replace "10G" with -- 106 --.

<u>Column 2,</u>
Line 42, replace "component" with -- components --.

<u>Column 4,</u>
Line 19, replace "ti" with -- t1 --.
Line 22, delete ":" after "control".

<u>Column 7,</u>
Line 37, replace "Stimulating" with -- stimulating --.

Signed and Sealed this

Thirteenth Day of January, 2004

JON W. DUDAS
*Acting Director of the United States Patent and Trademark Office*